United States Patent [19]
Berkoff et al.

[11] 4,079,061
[45] Mar. 14, 1978

[54] PROCESS USING ALKALI FUSION FOR DECYANATION OF TERT.-NITRILES

[75] Inventors: Charles E. Berkoff, Huntingdon Valley, Pa.; Donald E. Rivard, Medford Lakes, N.J.

[73] Assignee: SmithKline Corporation, Philadelphia, Pa.

[21] Appl. No.: 698,448

[22] Filed: Jun. 21, 1976

[51] Int. Cl.$^2$ ............................................ C07D 211/82
[52] U.S. Cl. ............................ 260/296 R; 260/293.69; 544/124; 260/570 R
[58] Field of Search .................... 260/296 R, 247.5 G, 260/293.69, 570 R

[56] References Cited
U.S. PATENT DOCUMENTS 3,116,297   12/1963   Kasper et al. .................... 260/296 R

OTHER PUBLICATIONS

Frankoski et al., Analytical Chemistry, vol. 44, pp. 2078 to 2080, (1972).

*Primary Examiner*—Henry R. Jiles
*Assistant Examiner*—Bernard Dentz
*Attorney, Agent, or Firm*—William H. Edgerton

[57] ABSTRACT

An improvement in the decyanation of tertiary nitriles comprises the alkali fusion of the nitriles. Exemplary are the preparation of chlorpheniramine and brompheniramine by heating the respective nitriles in liquid sodium or potassium hydroxide at from 100°–200°.

10 Claims, No Drawings

PROCESS USING ALKALI FUSION FOR DECYANATION OF TERT.-NITRILES

This invention relates to an improvement in the decyanation of organic nitriles and employs alkali fusion. In particular this new process is of value in the decyanation of α,α-diarylaminoalkylnitriles to produce ω,ω-diarylalkylamines having utility as antihistamines. It is of prime importance as a new commercial method for producing chlorpheniramine and bromopheniramine.

Prior art methods for decyanation involve using large excesses of sulfuric/hydrohalic acids or sodamide in toluene or xylene. Possibly the most pertinent prior art is U.S. Pat. No. 3,116,297 which discloses the use of potassium hydroxide in a water immisable organic solvent such as xylene, dichlorobenzene or cumene. To our knowledge the present method has not been previously applied to tertiary nitriles. Alkali fusion for decyanation of organic nitriles has been used only sparingly in the art and that for analytical purposes only such as the alkali fusion of polyacrylonitrile to give the amide then ammonia and a carboxylic acid salt; S. P. Frankoski et al., *Anal. Chem.* 44:2078-2080, 1972. A general review of other alkali fusion reactions is presented in K. W. Bentley, Technique of Organic Chemistry Vol. XI, pages 655-705, New York, Interscience (1963).

The term "alkali fusion" refers to a reaction in which an alkali metal hydroxide is used as a reactant and carrying medium in the liquid or fused state. Of course such alkali metal hydroxides are solid at room temperature.

The present improvement gives almost quantitative yields in its preferred embodiments, has a very simple work up procedure and very low mixture volumes which enables one to achieve a high total throughput in the reaction mixture. There is no evolution of carbon dioxide during the procedure. No organic solvents are used during the reaction procedure but only during work up which enables easy solvent recovery. Reaction time is remarkably decreased from the most useful prior art procedure, typically from 16–24 hours to from ½–5 hours.

The reaction conditions of this improvement are very simple. A mole ratio of nitrile to alkali of 1 to 1 up to a large excess of alkali is usable but for practical purposes a 4–8 mole excess of alkali is used. The temperature may vary from about 100°–200° C. with a preferred range of about 130–160° C. Times of reaction are from about ½–8 hours with 2–5 hours preferred. The course of the reaction may be monitored by LPC examination of an aliquot. At lower range of excess of alkali or lower temperatures longer reaction times are required while, on the other hand, over heating tends to give decomposition and subsequently lower yields. Most usefully potassium hydroxide is used with a 4–8 mole excess of alkali at about 150° C. Sodium or potassium hydroxide or mixtures thereof can be used. Often a mixture of sodium and potassium hydroxide can be used to help control the temperature of the reaction mixture.

The improvement can be applied to a large number of tertiary nitriles but is most useful in the following reaction:

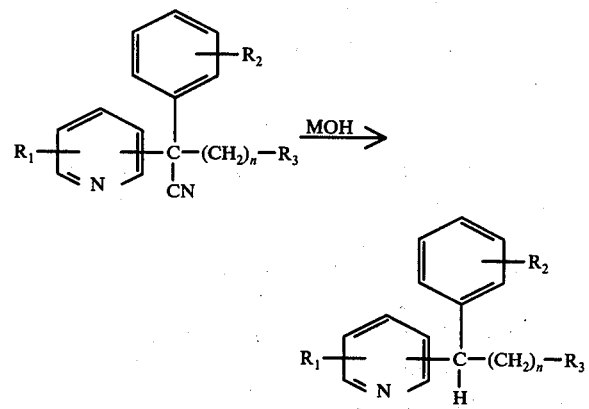

in which:
R₁ is hydrogen or lower alkyl;
R₂ is hydrogen, halo, lower alkyl, lower alkoxy, hydroxyl, amino, dilower alkylamino, nitro or carboxy;
R₃ is diloweralkylamino, N-morpholino or N-piperidino;
M is an alkali metal and
n is an integer of from 2–4.

Such lower alkyl or alkoxy groups contain conveniently from 1–6 carbons.

Preferably, the reaction is applied to the commercial products, chlorpheniramine and brompheniramine, which are those compounds above in which R₁ is hydrogen, the pyridyl ring is attached at position 2, R₂ is chloro or bromo at position 4, n is 2 and R₃ is dimethylamino.

The following examples are designed to teach the practice of this invention to those skilled in the art.

EXAMPLE 1

A mixture of 299.8 g. (1.0 m.) of chlorpheniramine nitrile[2-(4-chlorophenyl)-4-dimethylamino-2-(2-pyridyl)-butyronitrile] and 264 g. (4.0 m.) of potassium hydroxide pellets (85%) was heated to 150° C. over 15 minutes then held at 150° C. for 2 hours or more. The potassium hydroxide dissolves at about 110° C. The reaction mixture was efficiently stirred during heating.

The reaction mixture was cooled to 100° C. then toluene (300 ml.) added followed by 300 ml. of water. Stirring was continued until all the solids were dissolved. The aqueous layer was removed. The organic layer was removed and washed with 300 ml. of saturated salt water. The toluene extract was dried, the solvent taken off and the residue distilled to give a yield of 95–100% of chlorpheniramine (b.p. 140°–150° C. at 0.05 mm.) dependent on the purity of the starting material.

EXAMPLE 2

A mixture of 31 g. (0.09 m.) of brompheniramine nitrile [2-(4-bromophenyl)-4-dimethylamino-2-(2-pyridyl)-butyronitrile] and 29.7 g. (0.45 m.) of 85% potassium hydroxide was heated with stirring at about 150° C. for 1½ hours. After sampling the reaction mixture by vapor phase chromatography (V.P.C); the mixture was cooled and worked up with toluene-water to give 29 g. of crude residue. The residue was purified by distillation at 135°–160° C. at 0.025 mm. to give 17.5 g. (63.5%) of brompheniramine.

The base (13.6 g.) was reacted with 4.94 g. of maleic acid in 74 ml. of isopropanol at 35°–40° C. After recrystallization from isopropanol the desired maleate salt was obtained in 86.5%.

EXAMPLE 3

The procedure of the above examples is run on the following nitriles in the molar quantities noted:

4-dimethylamino-2-phenyl-2-(2-pyridyl)-butyronitrile (1 m.e.) with sodium hydroxide pellets (7 m.e.) gives 3-phenyl-3-(2-pyridyl)-N,N-dimethylpropylamine.

2-phenyl-4-piperidino-2-(2-pyridyl)-butyronitrile (1 m.e.) with potassium hydroxide pellets (6 m.e.) gives N-[3-phenyl-3-(2-pyridyl)-propyl]-piperidine.

2-phenyl-4-morpholino-2-(2-pyridyl)-butyronitrile (1 m.e.) with potassium hydroxide (9 m.e.) gives N-[3-phenyl-3-(2-pyridyl)-propyl]-morpholine.

2-(4-methoxyphenyl)-4-dimethylamino-2-(2-pyridyl)-butyronitrile (1 m.e.) with sodium hydroxide (5 m.e.) gives 3-(4-methoxyphenyl)-3-(2-pyridyl)-N,N-dimethylpropylamine.

2-(4-isopropylphenyl)-4-dimethylamino-2-(2-pyridyl)-butyronitrile (1 m.e.) with potassium hydroxide (6 m.e.) gives 3-(4-isopropylphenyl)-3-(2-pyridyl)-N,N-dimethylpropylamine.

2-(3-aminophenyl)-6-dimethylamino-2-(2-pyridyl)-capronitrile (1 m.e.) with potassium hydroxide (5 m.e.) gives 5-(3-aminophenyl)-5-(2-pyridyl)-N,N-dimethylpentylamine.

2-(4-nitrophenyl)-4-dimethylamino-2-(2-pyridyl)-butyronitrile (1 m.e.) with potassium-sodium hydroxides mixture (1-1 with total of 5 m.e.) gives 3-(4-nitrophenyl)-3-(2-pyridyl)-N,N-dimethylpropylamine.

EXAMPLE 4

The following runs on chlorpheniramine nitrile to give chlorpheniramine illustrates the versatility of this reaction:

| Nitrile (mole) | Potassium Hydroxide (mole) | Temp. C. | Time (hours) | Yield (%) |
|---|---|---|---|---|
| 1 | 8 | 120° | 6 | 85 |
| 1 | 1 | 120° | 6 | 65–75 |
| 1 | 8 | 200° | 1 | 95–100 |
| 1 | 1 | 200° | 5 | 85 |
| 1 | 7 | 150° | 3 | 95–97 |
| 1 | 6 | 150° | 3 | 95–97 |
| 1 | 5 | 150° | 3 | 95–97 |

What is claimed is:

1. In the method of decyanating $\alpha,\alpha$-diarylaminoalkynitriles, the improvement comprising the alkali fusion of said nitrile in sodium hydroxide or potassium hydroxide at a temperature selected from the range of about 100°–200° C. until decyanation is complete.
2. The method of claim 1 in which the nitrile is chlorpheniramine nitrile.
3. The method of claim 1 in which the nitrile is brompheniramine nitrile.
4. The method of claim 2 in which the temperature of the reaction is about 130°–160° C.
5. The method of claim 3 in which the temperature of the reaction is about 130°–160° C.
6. The method of claim 4 in which the mole ratio of alkali to nitrile is from 4 to 1 to 8 to 1.
7. The method of claim 6 in which the time of reaction is from about ½–8 hours.
8. The method of claim 7 in which the time of reaction is from about 2–5 hours.
9. The method of claim 8 in which the alkali metal is potassium hydroxide.
10. The method of claim 8 in which the alkali metal is a mixture of sodium hydroxide and potassium hydroxide.

* * * * *